United States Patent
Han et al.

(10) Patent No.: US 10,874,348 B1
(45) Date of Patent: Dec. 29, 2020

(54) FORCE SENSING FOR PPG HEART-RATE PERFORMANCE ENHANCEMENT AND CONTACT DETECTION

(71) Applicant: Apple Inc., Cupertino, CA (US)

(72) Inventors: Chin San Han, Mountain View, CA (US); Vivek Venugopal, San Jose, CA (US); Ueyn L. Block, Menlo Park, CA (US); Nicholas Paul Joseph Allec, Menlo Park, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 15/272,133

(22) Filed: Sep. 21, 2016

Related U.S. Application Data (60) Provisional application No. 62/235,216, filed on Sep. 30, 2015.

(51) Int. Cl.
 *A61B 5/00* (2006.01)
 *A61B 5/024* (2006.01)
 *A61B 90/00* (2016.01)

(52) U.S. Cl.
 CPC ........ *A61B 5/6843* (2013.01); *A61B 5/02427* (2013.01); *A61B 5/02438* (2013.01); *A61B 5/681* (2013.01); *A61B 5/721* (2013.01); *A61B 2090/065* (2016.02)

(58) Field of Classification Search
 CPC .............. A61B 5/6843; A61B 5/02427; A61B 5/02438; A61B 5/681
 See application file for complete search history.

(56) References Cited

U.S. PATENT DOCUMENTS

| | | | |
|---|---|---|---|
| 5,483,261 | A | 1/1996 | Yasutake |
| 5,488,204 | A | 1/1996 | Mead et al. |
| 5,825,352 | A | 10/1998 | Bisset et al. |
| 5,835,079 | A | 11/1998 | Shieh |
| 5,880,411 | A | 3/1999 | Gillespie et al. |
| 6,188,391 | B1 | 2/2001 | Seely et al. |
| 6,310,610 | B1 | 10/2001 | Beaton et al. |
| 6,323,846 | B1 | 11/2001 | Westerman et al. |
| 6,690,387 | B2 | 2/2004 | Zimmerman et al. |
| 7,015,894 | B2 | 3/2006 | Morohoshi |

(Continued)

FOREIGN PATENT DOCUMENTS

| | | |
|---|---|---|
| JP | 2000-163031 A | 6/2000 |
| JP | 2002-342033 A | 11/2002 |

OTHER PUBLICATIONS

Lee, S.K. et al. (Apr. 1985). "A Multi-Touch Three Dimensional Touch-Sensitive Tablet," *Proceedings of CHI: ACM Conference on Human Factors in Computing Systems*, pp. 21-25.

(Continued)

*Primary Examiner* — Tammie K Marlen
(74) *Attorney, Agent, or Firm* — Brownstein Hyatt Farber Schreck, LLP (57) ABSTRACT

The present disclosure generally relates to wearable devices and methods for measuring a photoplethysmographic signal. The wearable devices and methods may include a force sensor that provides input used for motion-noise filtering to obtain improved PPG signals. Feedback from the force sensor may also be used to indicate whether the amount of pressure exerted by the device should be adjusted, or whether the device should be switched to a locked state.

21 Claims, 9 Drawing Sheets

(56) References Cited

U.S. PATENT DOCUMENTS

| | | | |
|---|---|---|---|
| 7,184,064 | B2 | 2/2007 | Zimmerman et al. |
| 7,616,110 | B2 | 11/2009 | Crump et al. |
| 7,663,607 | B2 | 2/2010 | Hotelling et al. |
| 8,378,811 | B2 | 2/2013 | Crump et al. |
| 8,479,122 | B2 | 7/2013 | Hotelling et al. |
| 8,618,930 | B2 | 12/2013 | Papadopoulos et al. |
| 8,655,441 | B2 | 2/2014 | Fletcher et al. |
| 8,761,853 | B2 * | 6/2014 | Thaveeprungsriporn .................... G01N 21/3151 600/322 |
| 8,948,832 | B2 | 2/2015 | Hong et al. |
| 9,717,423 | B2 * | 8/2017 | Loseu .................. A61B 5/7207 |
| 2006/0197753 | A1 | 9/2006 | Hotelling |
| 2014/0155705 | A1 | 6/2014 | Papadopoulos et al. |
| 2015/0190063 | A1 | 7/2015 | Zakharov et al. |
| 2017/0172476 | A1 * | 6/2017 | Schilthuizen ...... A61B 5/14552 |
| 2017/0347957 | A1 * | 12/2017 | van den Ende ...... A61B 5/6843 |

OTHER PUBLICATIONS

Rubine, D.H. (Dec. 1991). "The Automatic Recognition of Gestures," CMU-CS-91-202, Submitted in Partial Fulfillment of the Requirements for the Degree of Doctor of Philosophy in Computer Science at Carnegie Mellon University, 285 pages.

Rubine, D.H. (May 1992). "Combining Gestures and Direct Manipulation," CHI ' 92, pp. 659-660.

Westerman, W. (Spring 1999). "Hand Tracking, Finger Identification, and Chordic Manipulation on a Multi-Touch Surface," A Dissertation Submitted to the Faculty of the University of Delaware in Partial Fulfillment of the Requirements for the Degree of Doctor of Philosophy in Electrical Engineering, 364 pages.

* cited by examiner

FORCE SENSING FOR PPG HEART-RATE PERFORMANCE ENHANCEMENT AND CONTACT DETECTION

CROSS-REFERENCE TO RELATED APPLICATIONS

This application claims priority to U.S. Provisional Patent Application Ser. No. 62/235,216, filed Sep. 30, 2015, which is hereby incorporated by reference in its entirety.

FIELD

The present disclosure relates generally to wearable devices and methods for measuring a photoplethysmographic signal. The wearable devices and methods may include a force sensor that can provide input used for motion-noise filtering during processing of the photoplethysmographic signal. Feedback from the force sensor may also be used to indicate whether the amount of pressure exerted by the device should be adjusted, or whether the device is off wrist.

BACKGROUND

The present disclosure relates generally to wearable devices and methods for measuring a photoplethysmographic signal. Soft tissue can transmit and reflect both visible and near-infrared radiation. Thus, if light is projected onto an area of skin and the transmitted and/or reflected light detected after its interaction with the skin, blood, and other tissues, time varying changes in light absorbance can be observed. This time varying light absorbance signal (photoplethysmographic or "PPG" signal) may be affected by a number of factors, some of which can include the optical properties of the tissues and blood at the measurement site, and the wavelength of the light source.

PPG signals can be used in many applications, such as heart rate and oxygen saturation determination, but can be susceptible to motion noise caused by, for example, movements of the user's body and/or internal tissue motion. Although forces created by bulk body movements can be detected by an accelerometer, flexion, for example, of the finger or hand can generate internal tissue forces within the wrist that, for a wrist-worn device, may not be detected by an accelerometer (e.g., flexion can occur while the limbs are stationary). Accordingly, systems and methods for PPG detection capable of detecting body movements and internal tissue forces can be beneficial.

SUMMARY

Disclosed herein are wearable devices for obtaining PPG signals that can include a force sensor capable of performing various functions. The wearable devices may comprise a housing, a PPG sensor configured to detect a PPG signal, a force sensor configured to detect a force signal, and a processor within the housing configured to run an algorithm using the detected PPG signal and force signal, where the algorithm uses the force signal to condition or disqualify the PPG signal. The force signal may correlate to an internal tissue force. Accordingly, in certain instances, the algorithm may condition the PPG signal by filtering the force signal from the PPG signal. When the force signal is above a maximum force threshold, the algorithm may disqualify the PPG signal from further processing. PPG signals that have been conditioned or not disqualified may then be used to provide data or information related to various physiological parameters, e.g., heart rate and/or oxygen saturation ($SpO_2$) of a user. In other instances, e.g., when the wearable device is a wrist-watch and the force signal is above a maximum force threshold, the wrist-watch may provide a notification or alert to the user to loosen the watch band. In this instance, loosening of the watch band may decrease the amount of noise generated by internal tissue forces.

The force sensor may be provided in any suitable location on the wearable device, and in some instances may be disposed between the housing and the PPG sensor. An accelerometer may also be included on or within the wearable devices to detect gross/bulk body movement. As used herein, the terms "force sensor" and "pressure sensor" are used interchangeably. The wearable devices may be configured to be worn on a user's wrist, for example, as a wrist-watch. In some variations, the wearable device can be a portable communications device, such as a mobile telephone, that also contains other functions, such as PDA and/or music player functions.

In instances when the wearable device is operated in a physiological signal mode (e.g., to obtain heart rate information), the force sensor can be configured to determine if internal tissue forces are being dynamically applied in the vicinity of a PPG sensor. These internal tissue forces can result in noise (e.g., motion artifacts) that can be mistaken for the target physiological signal, which in turn can lead to an erroneous determination of a user's physiological signals (e.g., pulse or heart rate). Incorporating a force sensor in the wearable device can help characterize local force dynamics and provide an avenue for determining whether a physiological signal is being corrupted by internal tissue motion (e.g., movement of tendons in the wrist). Information from the force sensor can be used to improve measurement accuracy by, for example, disqualifying motion-contaminated PPG signals and/or conditioning of the PPG signals by using the force sensor input (i.e., force signal) as the basis for motion-noise filtering. One or more force sensors configured to determine if internal tissue forces are being applied in the vicinity of a PPG sensor may be incorporated into the wearable device.

Additionally or alternatively, the wearable device may be operated in a contact mode, and the force sensor can be configured to determine whether the wearable device is in contact with the user's skin. Upon detecting contact, the wearable device can be switched into an unlocked state. When contact is not detected by the force sensor, the wearable device can be configured to turn the device into a locked state and/or a low power mode. Furthermore, the wearable device can be configured to process feedback from the force sensor that can indicate whether more or less force should be applied by the wearable device. In some examples, the force information can be used to determine whether a wrist-watch should be loosened or tightened, to optimize reading of a PPG signal. Additionally or alternatively, the force signal can provide information on whether the wearable device should be repositioned on a body area for better contact so that it may operate in a more desirable pressure range. The wearable device can include icons or other graphics on a display that indicate various operating modes selectable by the user, e.g., heart rate mode, contact mode, etc.

Methods for operating a wearable device are also disclosed herein. The methods generally include the steps of: operating the wearable device in a contact mode; detecting a force signal using a force sensor while the wearable device operates in the contact mode; operating the wearable device in a physiological signal mode; and detecting a PPG signal using a PPG sensor while the wearable device operates in the physiological signal mode. Thereafter, the PPG signal may be conditioned or disqualified using the force signal. Conditioning of the force signal may include filtering the force signal from the PPG signal. If the force signal is above a maximum force threshold, the PPG signal obtained during the same time period as the force signal may be disqualified. As previously stated, the force signal may correlate to an internal tissue force. Information that may be obtained during the physiological signal mode, include without limitation, heart rate and oxygen saturation of a user. The contact mode and physiological signal mode may be operated continuously, intermittently, simultaneously, or upon activation by a user. In some instances, if the detected force signal is below a minimum force threshold, the wearable device indicates to the user to increase the pressure from the wearable device against the user's skin. For example, when the wearable device is a wrist-watch, the band of the wrist-watch can be tightened.

Methods for obtaining PPG signals of a user are further disclosed herein. The methods generally include the steps of: attaching a wearable device to the user, the wearable device comprising a PPG sensor system and a force sensor; detecting a PPG signal using the PPG sensor system; and detecting a force signal using the force sensor. The PPG signal may be conditioned by filtering the force signal from the PPG signal or the PPG signal disqualified if the force signal is above a predetermined threshold, e.g. a maximum force threshold, as previously stated. The force signal may correlate to an internal tissue force. The PPG signal may provide information related to, e.g., the heart rate or oxygen saturation, of the user. The wearable device may be a wrist-watch.

The methods described above may generally be used to improve the quality of the PPG signal. Additionally, and as previously stated, information from the force sensor can be input into an algorithm operable to determine whether the wearable device is in a worn or an unworn state, e.g., an "on wrist" or "off wrist" state. If feedback from the force sensor indicates that the wearable device is in an unworn state, the method may further comprise the step of turning the device to a locked state or low power mode to, e.g., prolong its battery life and promote device efficiency.

The terminology used in the description of the various described embodiments herein is for the purpose of describing particular embodiments only and is not intended to be limiting. As used in the description of the various described embodiments and the appended claims, the singular forms "a", "an," and "the" are intended to include the plural forms as well, unless the context clearly indicates otherwise.

It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

DESCRIPTION OF THE FIGURES

For a better understanding of the various described embodiments, reference should be made to the Detailed Description below, in conjunction with the following drawings in which like reference numerals refer to corresponding parts throughout the figures.

DETAILED DESCRIPTION

The following description sets forth exemplary wearable devices, methods for operating the devices, and methods for obtaining a PPG signal. It should be recognized, however, that such description is not intended as a limitation on the scope of the present disclosure but is instead provided as a description of exemplary embodiments.

Described herein are wearable devices capable of obtaining PPG signals and detecting contact of the wearable devices to the skin of a user. The wearable devices can comprise a housing, a PPG sensor configured to detect a PPG signal, a force sensor configured to detect a force signal, and a processor within the housing configured to run an algorithm using the detected PPG signal and force signal. In some variations, filtering or conditioning to remove all or part of the force signal from the PPG signal may help to improve quality of the PPG signal. In other variations, the PPG signal may be improved by disqualifying that portion of the PPG signal obtained over the same period when a maximum force signal is detected. Additionally, and as further described below, the force signal can be used to detect a worn (e.g., on wrist) or unworn (e.g., off wrist) state by the user, or whether more pressure should be applied by the wearable device against the skin.

The wearable device may be any electronic device suitable for contact with a user's skin, e.g., a phone, wristwatch, arm or wrist band, headband, or any device for collecting biometric information, PPG signals, or other types of physiological signals. The wearable device may be worn on a wrist, ankle, head, chest, leg, etc., with the use of a band that is flexible and capable of adjustably fitting a user. For example, the band may be made from a flexible material or have a structure that allows it to have an adjustable circumference. In one variation, the wearable device is a wristwatch.

The housing of the wearable devices may be configured to have any size and shape suitable for the body area of contact and/or the indication of use, and may include a housing comprising an upper surface, a back (lower) surface, and side surfaces, an interior enclosed within the surfaces, and a display that is mounted in the upper surface of the housing. The display may, for example, be a touch screen or may be a display that is not touch sensitive. The display may include image pixels formed from light-emitting diodes (LEDs), organic LEDs (OLEDs), plasma cells, electrowetting pixels, electrophoretic pixels, liquid crystal display (LCD) components, or other suitable image pixel structures.

In some variations, the wearable device is a device where operation of a predefined set of functions on the device is performed exclusively through a touch screen. By using a touch screen as the primary input control device for operation, the number of physical input control devices (such as push buttons, dials, and the like) on the wearable device may be reduced. The predefined set of functions that are performed exclusively through a touch screen optionally include navigation between user interfaces/modes, e.g., contact and PPG signal modes. In one variation, the touchpad, when touched by the user, navigates the wearable device to a main, home, or root menu from any user interface/mode that is displayed on device. In such variations, a "menu button" is implemented using a touch screen.

The display may include icons or other graphics that indicate various operating modes selectable by the user, e.g., heart rate mode, contact mode, etc. A graphics module included in the housing may employ various known software components for rendering and displaying graphics on the touch screen or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like. In some variations, the graphics module stores data representing graphics to be used. Each graphic is, optionally, assigned a corresponding code. Here the graphics module receives, from applications etc., one or more codes specifying graphics to be displayed along with, if necessary, coordinate data and other graphic property data, and then generates screen image data to output to a display controller.

The housing, which may sometimes be referred to as a case, may be formed of plastic, glass, ceramics, fiber composites, metal (e.g., stainless steel, aluminum, etc.), other suitable materials, or a combination of these materials. In some variations, the housing or parts thereof may be formed from dielectric or other low-conductivity material. In other variations, the housing or at least some of the structures that make up the housing may be formed from metal elements.

A display cover layer such as a layer of cover glass or a transparent plastic layer may cover the surface of display. The display cover layer may have one or more openings. Windows may be provided in the display cover layer to allow light to pass through the display cover layer in connection with the operation of a light sensor, camera, or other optical component.

The wearable devices may also include one or more photoplethysmographic (PPG) sensors. A PPG signal can be measured by PPG sensors to derive corresponding physiological information (e.g., heart rate). Such PPG sensors can be designed to be sensitive to changes in the type of blood (e.g. oxygenated vs. deoxygenated) or amount of blood in a user's tissue that can result from fluctuations in the amount of blood oxygen or the volume of blood contained in the vasculature of a user.

In a basic form, PPG sensors can employ a light source or light emitter that illuminates the user's tissue and a light detector (photodetector) that receives light that reflects and/or scatters and exits the tissue. The PPG signal is typically the amplitude of the reflected and/or scattered light that is modulated with respect to certain properties of blood in the tissue. Exemplary light emitters include without limitation, light emitting diodes (LEDs), incandescent lights, and fluorescent lights. The LED may be a green LED, red LED, an infrared (IR) LED, or may be configured to emit at one or more predetermined wavelengths (e.g., green and red) of a set of wavelengths. When more than one light emitter is used, the plurality can include the same or different light emitters (with different emission wavelengths). For example, a combination of one or more green LEDs and IR LEDs may be used. In some variations, the light emitting diodes emit light with a peak spectral response between about 400 and 600 nm.

The PPG sensors may be provided and arranged in any suitable location(s) on the wearable device. In one variation, one or more PPG sensors are disposed on the back surface of the wearable device housing. In another variation, one or more PPG sensors are disposed on a side surface of the wearable device housing. PPG sensors may also be provided on a combination of surfaces, e.g., the back surface and a side surface of the wearable device housing. In yet further variations, one or more PPG sensors can be provided on an attachment mechanism of the wearable device. For example, when the wearable device is a wrist-watch, one or more of the PPG sensors can be disposed on the back and/or side surface of the wrist-watch housing. Alternatively or additionally, one or more PPG sensors can be disposed on the attachment mechanism of the watch, e.g., the wrist band.

The wearable devices may also include a single photodetector or a plurality of photodetectors. The photodetectors may be provided and arranged in any suitable location(s) on the wearable device. In one variation, one or more photodetectors are disposed on the back surface of the wearable device housing. In another variation, one or more photodetectors are disposed on a side surface of the wearable device housing. Photodetectors may also be provided on a combination of surfaces, e.g., the back surface and a side surface of the wearable device housing. In yet further variations, one or more photodetectors can be provided on an attachment mechanism of the wearable device. For example, when the wearable device is a wrist-watch, one or more of the photodetectors can be disposed on the wrist band. Similarly, one or more photodetectors can be disposed on the attachment mechanism of the watch, e.g., the wrist band. The photodetector typically generates an electrical current that is proportional to the amount of light detected. Another detector may be provided to convert the electrical current from the photodetector to a voltage that is proportional to the current.

The light emitter(s) may emit light having one or more wavelengths that are specific or directed to a type of physiological data to be collected. In one variation, the light emitter(s) emit light having one or more wavelengths specific to the collection of PPG signals. Similarly, the photodetectors may sample, measure and/or detect one or more wavelengths that are also specific or directed to a type of physiological data to be collected, e.g., a PPG signal for determination of heart rate. For instance, a light source emitting light having a wavelength in the green spectrum and a photodiode positioned to sample, measure, and/or detect a response or reflection corresponding with such light may provide data that may be used to determine or detect heart rate. In other variations, a light source emitting light having a wavelength in the red spectrum and a light source emitting light having a wavelength in the infrared spectrum and a photodetector positioned to sample, measure and/or detect a response or reflection of such light may provide data used to determine or detect $SpO_2$. In some examples, the light emitter(s) can emit infrared and/or red light for heart rate detection, while the light emitter(s) (or a different light emitter(s)) can emit green light to determine or detect $SpO_2$.

The PPG signal may be compromised by noise due to artifacts. Artifacts resulting from, for example, internal tissue motion (such as from tendon and muscle forces) can introduce noise into the signal, as described above. By including a force sensor on the wearable device, internal tissue motion noise can be detected and either filtered or disqualified from the PPG signal.

The force sensor may be any suitable sensor that is capable of sensing an applied force or pressure to a body part. Exemplary types of force sensors include without limitation, optical, mechanical, capacitive, piezoresistive, piezoelectric, and magnetic sensors. The force sensors may comprise a thin film flexible printed circuit, a flexible membrane or film, a strain-gauge, a load cell, piezoelectric material, ferromagnetic material, optical fibers, foil layers, electrodes, or combinations thereof.

One or more force sensors may be provided with the wearable device. For example, a plurality of force sensors may be configured as an array on or within the device. The force sensor can be disposed in any suitable location, and arranged in any suitable manner on the wearable device. In some variations, the force sensor can be disposed in the back surface of the wearable device housing. For example, the force sensor can be incorporated into a back plate that is coupled to and forms part of the device housing. In other variations, the back plate may be coupled to the housing, but the force sensor is positioned at one or more connection points between the back plate and the housing to measure the force that is applied between the back plate and housing (i.e., via forces applied to the back plate). In further variations, there may be a back plate with a force sensor between it and the rest of the housing, but the optical sensors, e.g., the PPG sensors, may not be incorporated into the plate (e.g., they may be incorporated into a second plate or another portion of the housing). In some instances, the force sensor may be on an external surface of the housing (e.g., on the external surface of the back plate) such that it can measure force directly applied to the sensor.

Figure 1A:
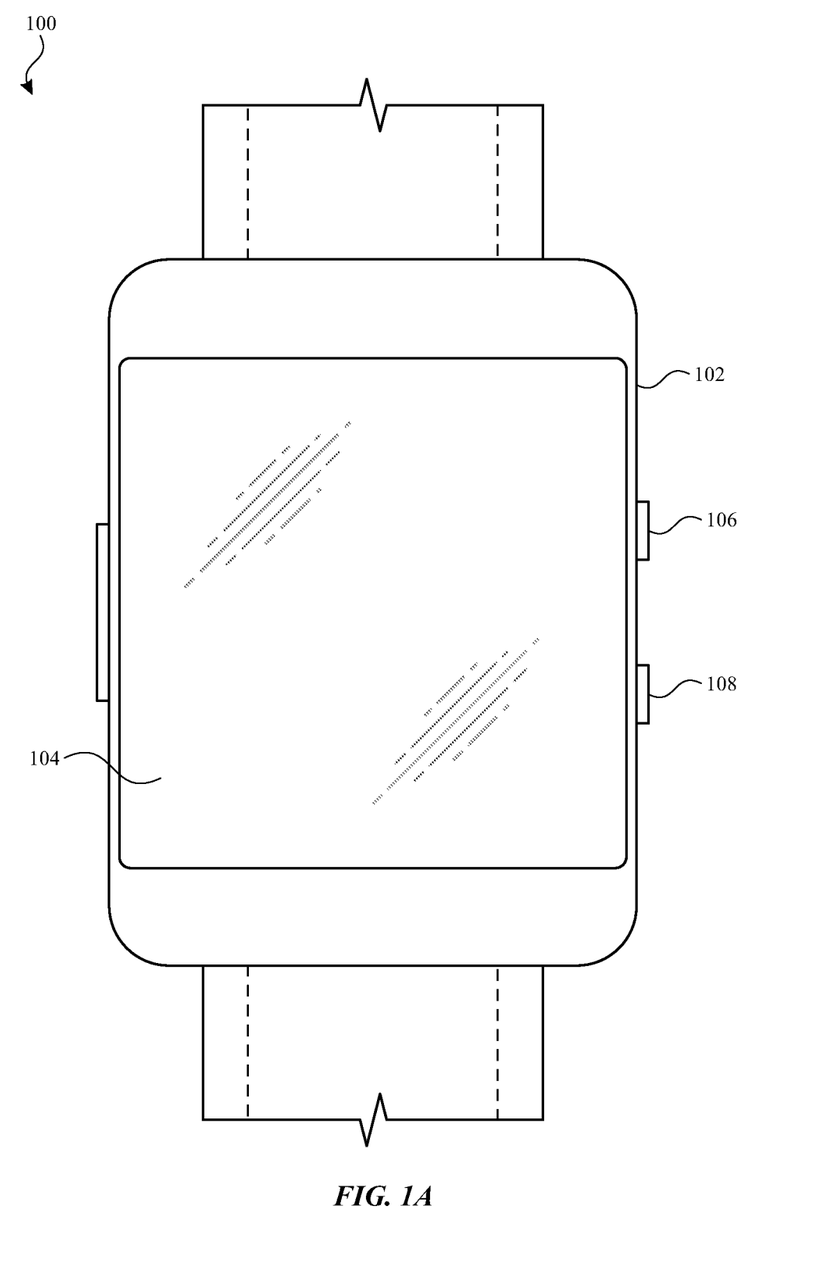
FIG. 1A depicts an exemplary wearable device according to examples of the disclosure.

Referring to FIG. 1A, an exemplary wearable device 100 is shown. Device 100 can include a housing 102 and a touch-sensitive display screen, such as touch screen 110. Alternatively, or in addition to touch screen 110, device 100 can have a display and a touch-sensitive surface. Touch screen 110 can include one or more intensity sensors for detecting intensity of contacts (e.g., touches) being applied. The one or more intensity sensors of touch screen 110 can provide output data that can represent the intensity of touches. The user interface of device 100 can respond to touches based on their intensity, meaning that touches of different intensities can invoke different user interface operations on device 100.

Figure 2:
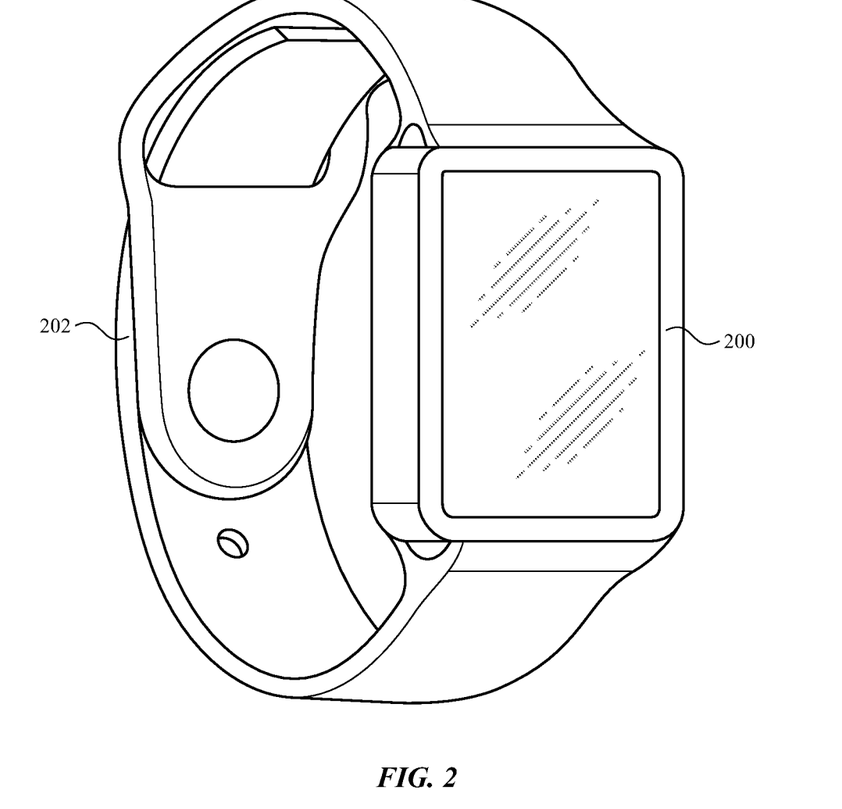
FIG. 2 depicts a perspective view of an exemplary wearable device having a strap for attaching the device to a user according to examples of the disclosure.

In some variations, device 100 can have one or more input mechanisms 106 and 108. Input mechanisms 106 and 108, if included, can be physical components or interfaces. Examples of physical input mechanisms can include push buttons and rotatable mechanisms. Device 100 can have one or more attachment mechanisms. Such attachment mechanisms, if included, can permit attachment of device 100 with, for example, hats, headbands, eyewear, earrings, necklaces, shirts, jackets, bracelets, watch straps, chains, trousers, belts, shoes, purses, backpacks, and so forth. These attachment mechanisms can permit device 100 to be worn by a user. Exemplary attachment mechanisms include without limitation, bands that may be secured to the user through the use of hooks and loops (e.g., Velcro), a clasp, and/or a band having memory of its shape, e.g., through the use of a spring metal band. For example, referring to FIG. 2, a wearable device 200 is shown including a band or strap 202 for attaching device 200 to a body area (e.g., a wrist) of a user.

Figure 1B:
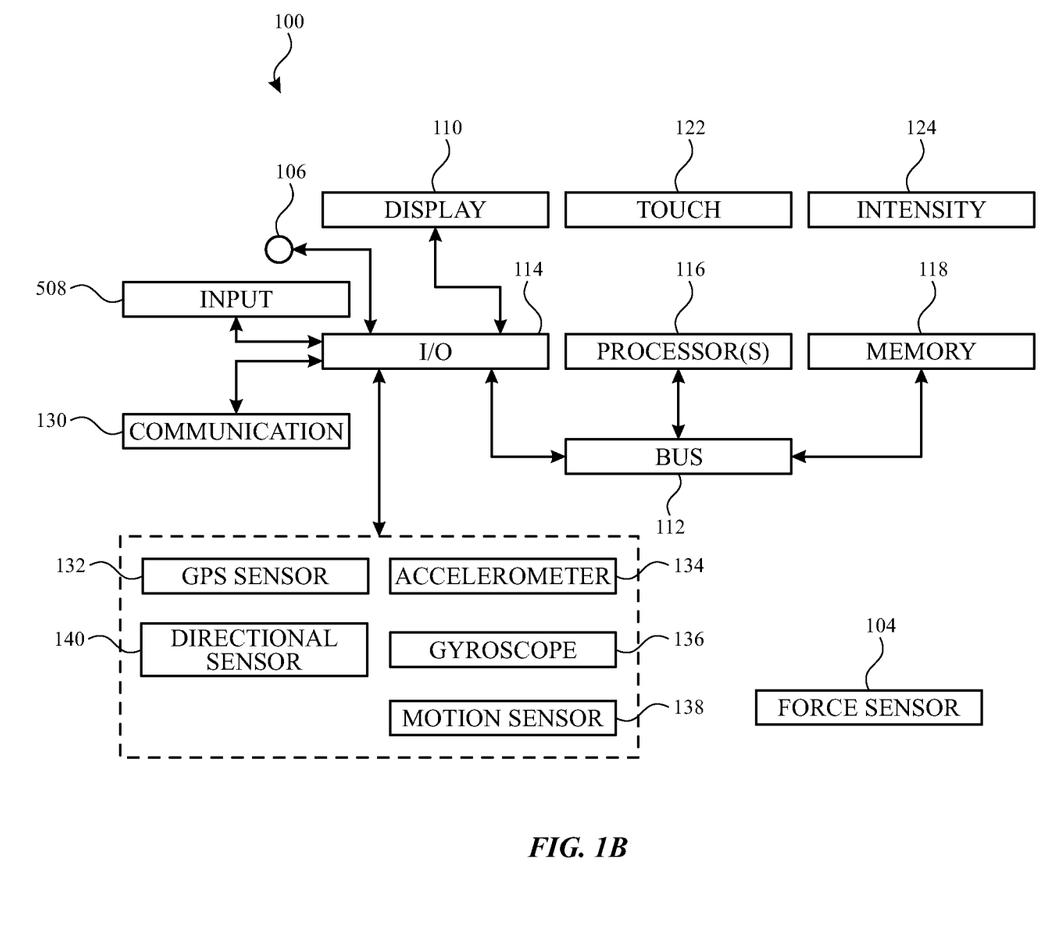
FIG. 1B is a block diagram showing the components of the wearable device in FIG. 1A according to examples of the disclosure.

FIG. 1B provides further details of the components of wearable device 100. Here device 100 can have bus 112 that operatively couples I/O section 114 with one or more computer processors 116 and memory 118. I/O section 114 can be connected to display 110, which can have touch-sensitive component 122 and, optionally, touch-intensity sensitive component 124. In addition, I/O section 114 can be connected with communication unit 130 for receiving application and operating system data, using Wi-Fi, Bluetooth, near field communication (NFC), cellular, and/or other wireless communication techniques. Device 100 can include input mechanisms 106 and/or 108. Input mechanism 106 may be a rotatable input device, a depressible and rotatable input device, for example. Input mechanism 108 may be a button, in some examples.

Wearable device 100 can include various sensors, such as GPS sensor 132, accelerometer 134, directional sensor 140 (e.g., compass), gyroscope 136, motion sensor 138, sensors for detecting various types of physiological information, e.g., temperature, and/or a combination thereof, all of which can be operatively connected to I/O section 114.

Memory 118 of wearable device 100 can be a non-transitory computer-readable storage medium, for storing computer-executable instructions, which, when executed by one or more computer processors 116, for example, can cause the computer processors to perform the algorithms further described below. The computer-executable instructions can also be stored and/or transported within any non-transitory computer-readable storage medium for use by or in connection with an instruction execution system, apparatus, or device, such as a computer-based system, processor-containing system, or other system that can fetch the instructions from the instruction execution system, apparatus, or device and execute the instructions. For purposes of this document, a "non-transitory computer-readable storage medium" can be any medium that can tangibly contain or store computer-executable instructions for use by or in connection with the instruction execution system, apparatus, or device. The non-transitory computer-readable storage medium can include, but is not limited to, magnetic, optical, and/or semiconductor storages. An example of such storage includes persistent solid-state memory such as flash, solid-state drives, and the like. It is understood that wearable device 100 is not limited to the components and configuration of FIGS. 1A and 1B, but can include other or additional components in multiple configurations.

Figure 3A:
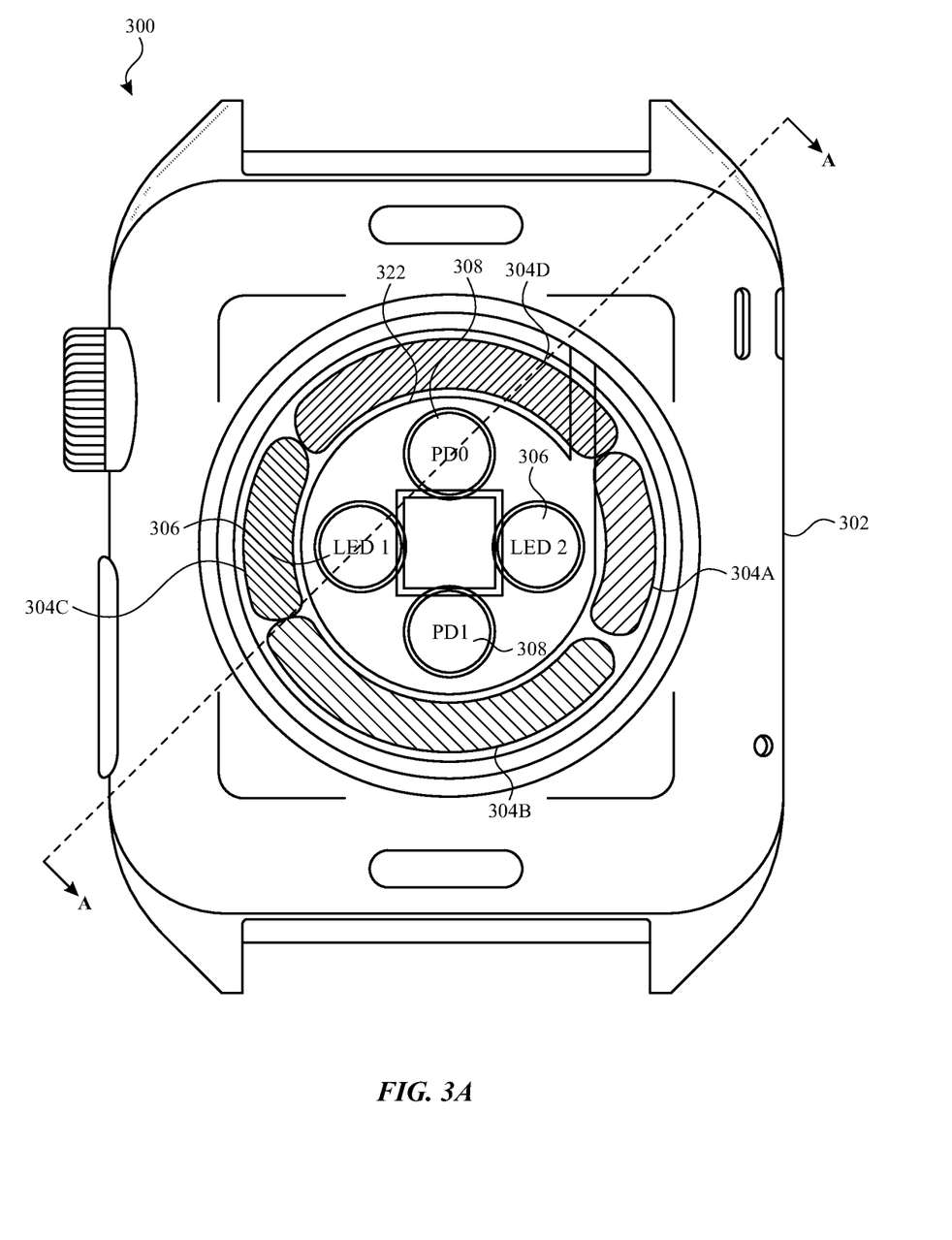
FIG. 3A depicts a top view of an exemplary wrist-watch including PPG sensors and a force sensor according to examples of the disclosure.
Figure 3B:
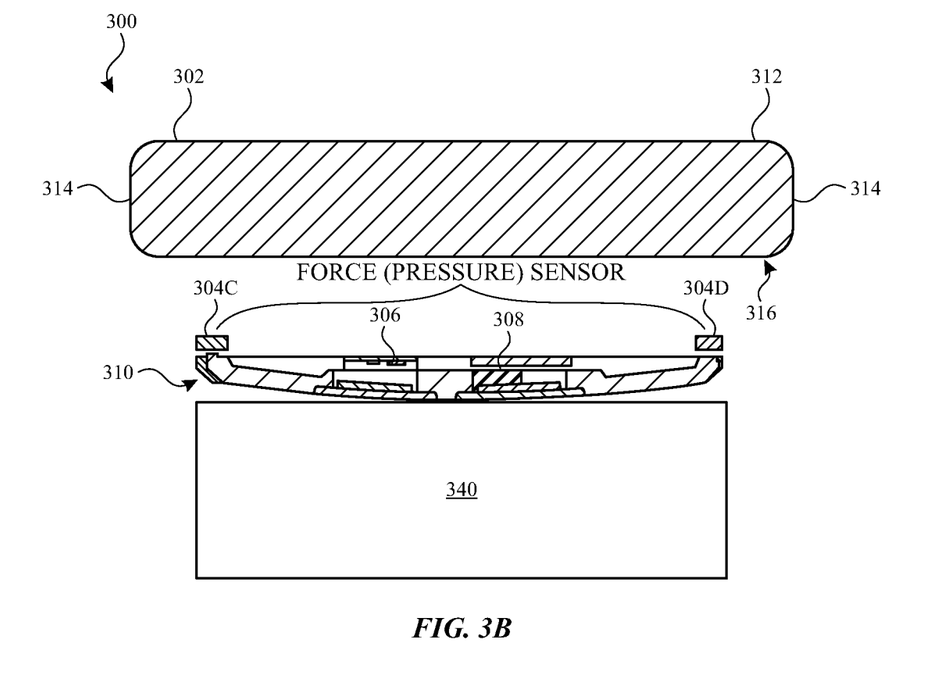
FIG. 3B shows side, cross-sectional view along line A-A of the wrist-watch in FIG. 3A according to examples of the disclosure.

For example, when the wearable device is a wrist-watch that includes a PPG sensor and a force sensor, the components may be configured as shown in FIGS. 3A-3B. In FIG. 3A, wrist-watch 300 can include housing 302. Coupled to the housing 302 can be one or more force sensors, such as force sensor 304a, force sensor 304b, force sensor 304c, and force sensor 304d, and a PPG sensor system 322. PPG sensor system 322 can include light emitters 306 and photodetectors 308. In some examples, force sensing can include one or more sensors located around the perimeter of device 300. For example, force sensor 304a and force sensor 304b can be located near light emitter LED 2 and photodetector PD 1, respectively, and force sensor 304c and force sensor 304d can be located near light emitter LED 1 and photodetector PD 0, respectively. Although four light emitters and two photodetectors are shown in the figure, examples of the disclosure can include any number of light emitters and photodetectors. In some examples, each force sensor can be operatively coupled to a separate optical component (e.g., light emitter or photodetector) as the other force sensors included in device 300. Furthermore, the light emitters and photodetectors can be provided in any suitable location within or on a surface of the housing or on an attachment mechanism (e.g., a watch strap or band).

Referring to FIG. 3B, which illustrates a cross-sectional view taken along line A-A of the wrist-watch provided in FIG. 3A, housing 302 can include upper surface 312, back surface 316, and side surfaces 314. Device 300 can include back plate 310, which force sensor 304a, force sensor 304b, force sensor 304c, and force sensor 304d can be disposed on. In some examples, force sensor 304a, force sensor 304b, force sensor 304c, and force sensor 304d can be located between housing 302 and back plate 310. Although the figure illustrates a gap located between back plate 310 and housing 302, examples of the disclosure can include back plate 310 touching back surface 316 of housing 302. The force sensors can be disposed between back plate 310 and back surface 316 of housing 302. In some examples, the back plate and housing can collectively define the back surface 316 of device 300.

In some instances, internal tissue force can applied pressure to back plate 310. Back plate 310 can transfer the applied force to the force sensors. The force sensors can detect the applied force (e.g., internal tissue force) and can generate a signal (e.g., a "force" signal) indicative of the amount of force applied. In some examples, the force signal can indicate whether or not a force has been applied without any information about the amount of force applied.

In some examples, each of the force sensors can be independently operable (e.g., independently biased) such that each sensor can measure different regions (e.g., left side) of device 300 subject to force. Each force sensor can be capable of discerning different amounts of force applied to different regions of device 300 and/or different amount of internal forces in skin 340. For example, more force may be applied to one side (e.g., left side, closest to where LED1 can be located) than another side (e.g., right side, closest to where LED2 can be located). Force sensor 304c can generate a force signal with a higher intensity than force sensor 304a.

In some examples, one or more edges of device can be located proximate to one or more anatomical features, which may distort (e.g., include motion artifacts) the measurement. The anatomical feature(s) can be detected using one or more of the force sensors. In response to the detected anatomic feature(s), the device can prompt the user to adjust (e.g., move the device body in a specific direction away from the anatomical feature(s)) the body of the device. For example, a force sensor located on a side (or a corner) (e.g., the side with the crown) of the device can detect a high pressure (i.e., an amount of pressure greater than a predetermined threshold), which may indicate that the side is located too close to a styloid. The device can prompt the user (e.g., using a display included in the device) to move the device by a specified distance (e.g., 3 mm) in a specific direction away from the styloid.

In some examples, one or more (e.g., at least two) force sensors can be electrically coupled together (e.g., by way of one or more switches (not shown)) can be configured to generate an aggregate force signal that can be sent to a processor, where the aggregate force signal of the electrically coupled force sensors can be equal to the sum of the individual force signals. In some examples, two force sensors can be measured and the differential between the force sensors can be sent to a processor for determining one or more physiological information of the user.

A processor (not shown) may be included in the housing and can be configured to run various algorithms based on information obtained from the PPG sensor system and/or the force sensor. In some variations, information/data obtained by the PPG sensor or wearable device may be transmitted to a remote location (e.g., a computer or a remote server). An antenna and wireless circuitry may be included in the wearable devices. The wireless circuitry can include, without limitation, cellular, LAN (local area network), or personal area network circuitry (e.g., Bluetooth), or combinations thereof.

The wearable devices disclosed herein may be generally used to obtain PPG signals from a user. The obtained PPG signals may then be used to extrapolate various types of physiological information/data. In some variations, the PPG signal is used to obtain information related to the heart rate of a user.

PPG signals can be susceptible to motion noise caused by internal tissue motion that can scatter light emitted by the light emitters. Force sensor 304a, 304b, 304c, and/or 304d, located in the vicinity of the PPG sensor (e.g., PD0 or PD1) may be able to characterize local force dynamics and provide a way to determine whether PPG signals are being corrupted by force-related (e.g., pressure-related) motion. This information can be used to improve PPG signal reporting by, for example, disqualifying motion-contaminated PPG signals and/or conditioning the PPG signal by using the force sensor input as the basis for motion-noise filtering.

Figure 3C:
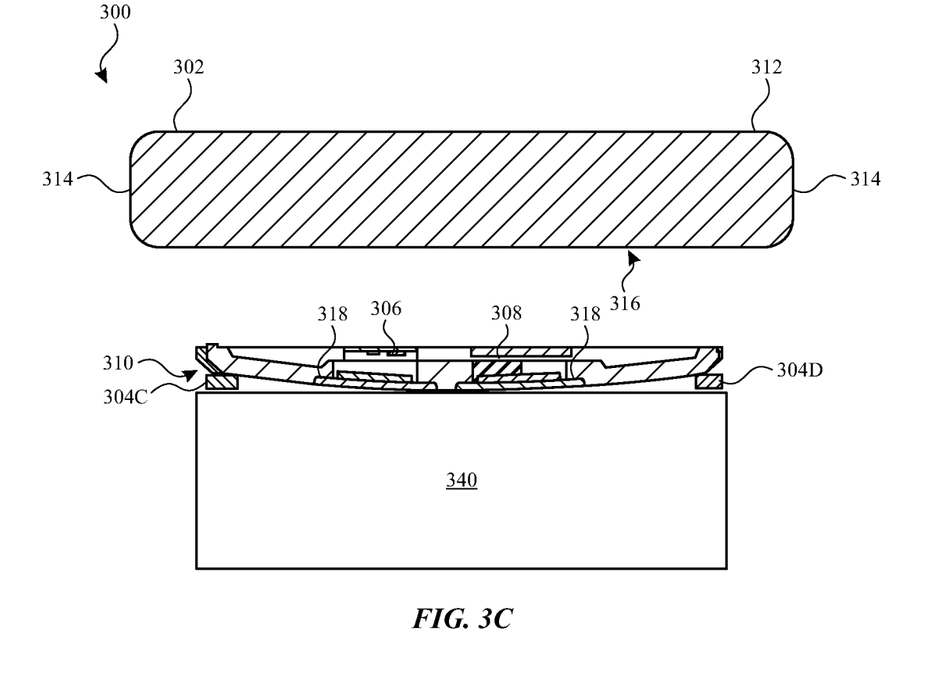
FIG. 3C illustrates an exemplary device including force sensors located between the back plate and the user according to examples of the disclosure.

In some examples, the one or more force sensors can be located closer to skin 340 such that transfer of force through back plate can be avoided. FIG. 3C illustrates an exemplary device including force sensors located between the back plate and the user according to examples of the disclosure. Force sensor 304a, force sensor 304b, force sensor 304c, and force sensor 304d can be disposed on back plate 310. In some examples, the force sensors can form a protrusion from device 300. In some examples, the force sensors can be flush with the cover structures 318.

Figure 4A:
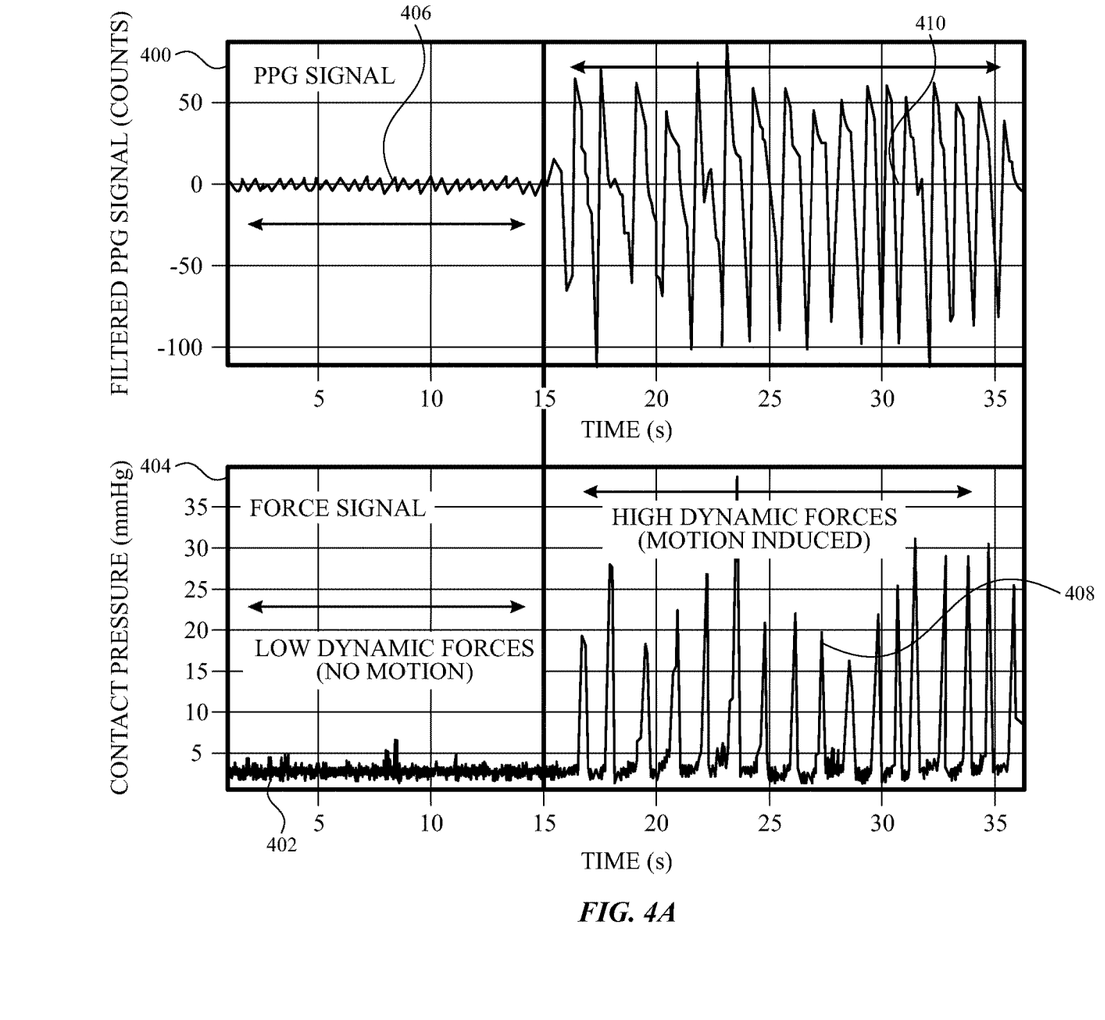
FIG. 4A illustrates exemplary PPG and force signals obtained from a wrist-worn device according to examples of the disclosure.
Figure 4B:
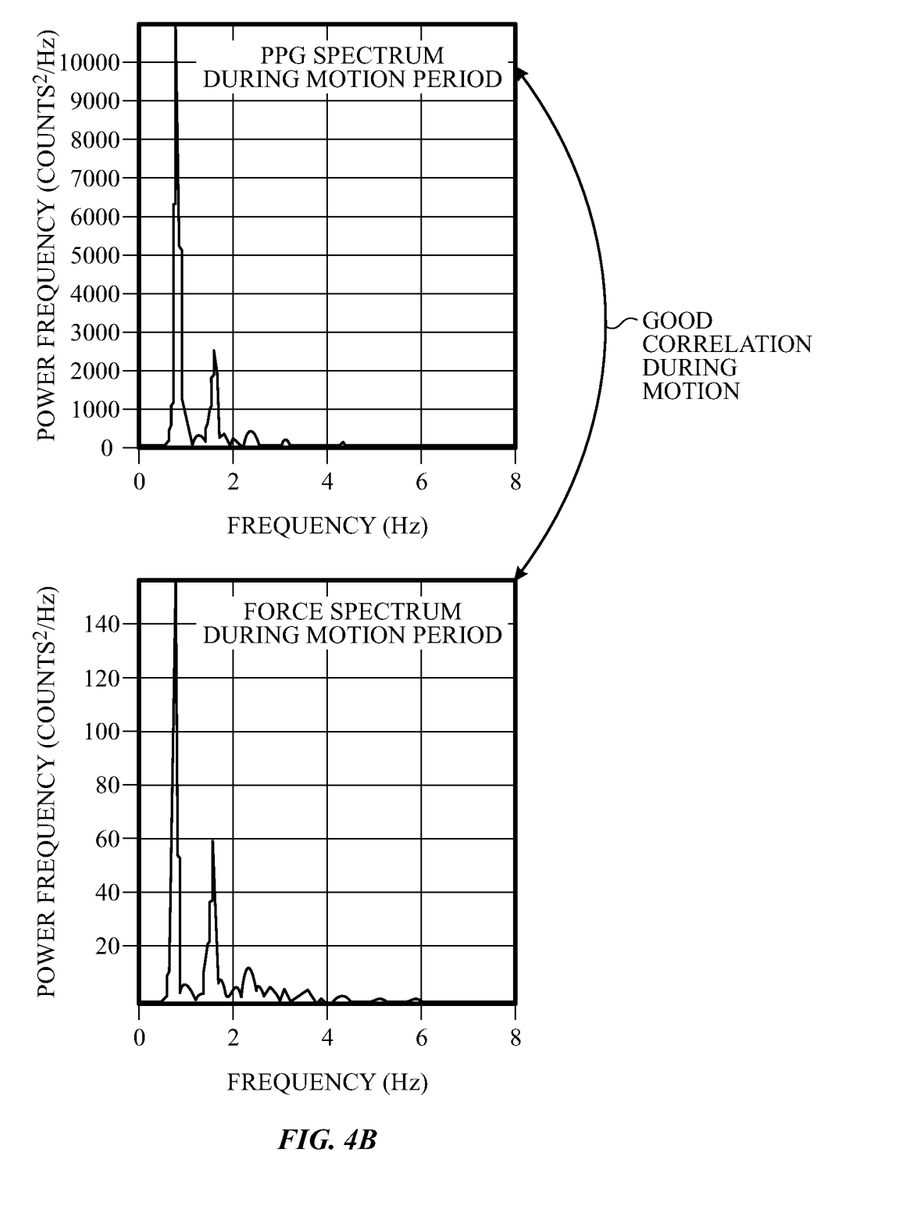
FIG. 4B provides data showing that a force signal can be correlated with internal tissue motion-noise artifacts according to examples of the disclosure.

Referring to FIG. 4A, exemplary PPG (e.g., heart rate) and force signals that have been recorded simultaneously from a wrist-worn device are provided. The PPG graph 400 illustrates that when the user begins with their wrist in a static position, i.e., no or low dynamic force signal 402 as shown in the force graph 404, the PPG signal 406 is a clear pulsatile signal with no motion artifact. When motion artifact is introduced by the user articulating their hands and fingers, a higher force signal 408 is detected that can mask the PPG signal (shown as motion-corrupted PPG signal 410). However, because motion-noise artifacts (such as internal tissue motion) can be correlated with the force signal, the reporting algorithm can be configured to either disqualify PPG signals during time periods when there are large dynamic forces, or use the force sensor signal to compensate for the motion noise and filter the force signal from the PPG signal. FIG. 4B provides data supporting the good correlation between the force signal and artifacts due to internal tissue motion. A processor may be provided in the wearable device housing configured to run the various algorithms for disqualifying and/or filtering the force signal.

The force signal may also be used to determine whether the amount of pressure exerted by the wearable device should be adjusted so that it can operate in a more desirable pressure range. For heart rate applications, when the amount of external applied force is lower than arterial pressure at the measurement site, the arterial pressure will generally be too low to obtain an adequate measurement, and a low PPG signal will be obtained. In contrast, when too much external force is applied, the blood vessels may become occluded at the measurement site, which may also result in an inaccurate PPG signal reading. Thus, to obtain an improved PPG signal, external pressure from the wearable device may be applied in an amount that is equal to arterial pressure. When equalization of pressure occurs, blood vessel (e.g., arterial capillary) diameter is constant at the measurement site, and the blood volume within the vessel at the measured region is typically unchanged. In some variations, the force signal may be used to provide information on whether the wearable device should be repositioned on a body area. In other variations, the force signal may be used to provide information on whether the amount of pressure exerted by the wearable device should be decreased. In yet further variations, the force signal may be used to provide information on whether the amount of pressure exerted by the wearable device should be increased. For example, when the wearable device is a wrist-watch, the force signal may be used to provide information on whether the wrist band should be loosened or tightened.

The acquisition of a strong heart rate (PPG) signal may be indicated to the user on the display of the wearable device. Heart rate may be indicated in any suitable manner by the wearable device. For example, heart rate may be indicated as a numerical value, a picture, or text on the device display, or be audibly provided by the wearable device. Heart rate may be indicated by combinations of any of the foregoing. In some variations, the wearable device may include a signal-strength indicator that is represented by the pulsing of an LED viewable by the user. Some implementations of the wearable device may use a light such as an LED to display the heart rate of the user by modulating the amplitude of the light emitted at the frequency of the user's heart rate. Other types of physiological data may be indicated in the same manner. Notifications relating to the obtained heart rate or other physiological data can also indicated in the same manner. In further variations, feedback from the force sensor may be used to determine whether the device is not being worn, e.g., the device is off wrist, and is being switched to a locked state. An audible or visible indicator may be provided by the wearable device upon a change in state, e.g., worn to unworn and/or unworn to worn.

A processor may be included in the wearable device and be configured to execute algorithms for carrying out the various methods described herein and control the reception and manipulation of input and output data between components of wearable device, e.g., the light emitters, photodetectors, and force sensor(s). The processor can be a single-chip processor or can be implemented with multiple components.

The wearable devices may also include a power system for powering the various components. The power system may include a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Figure 5A:
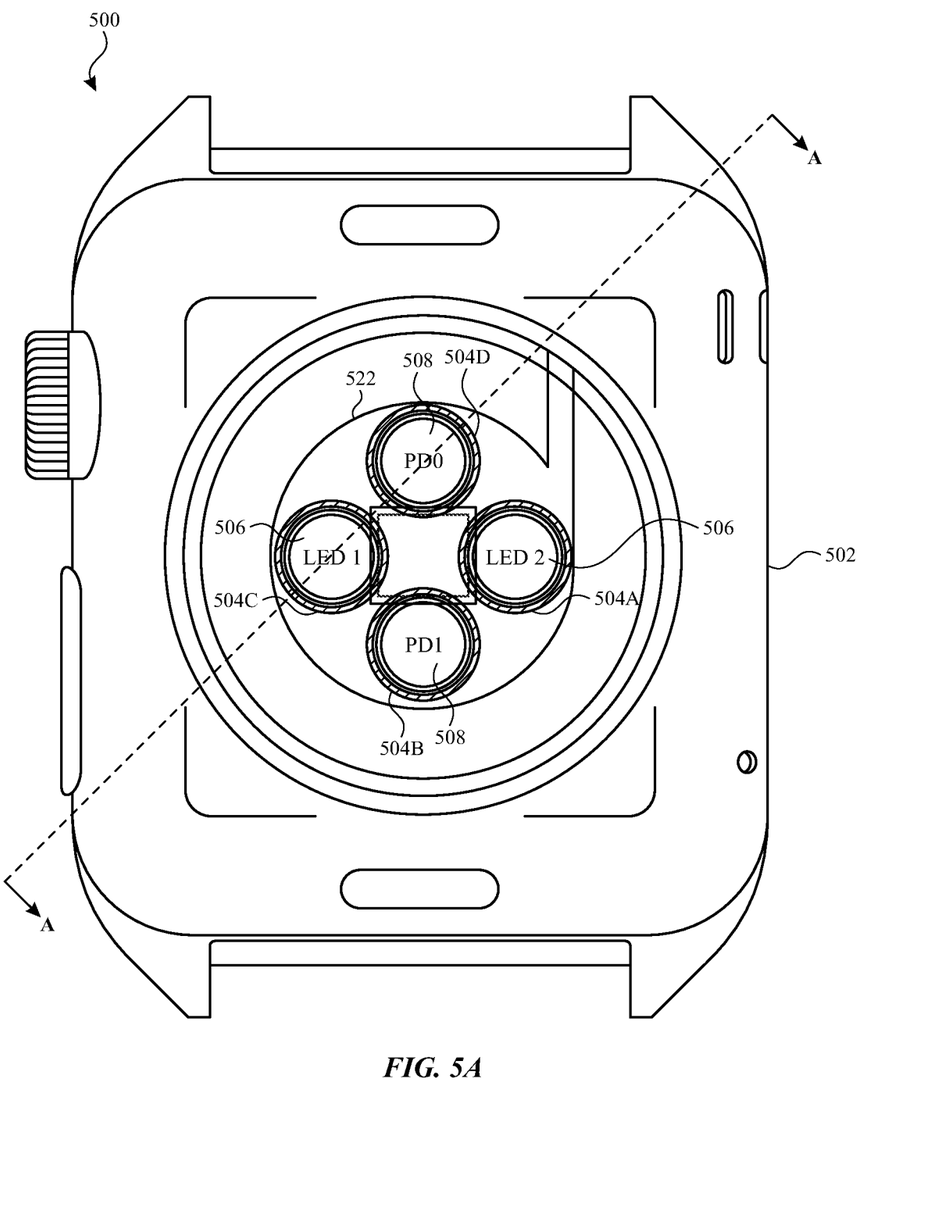
FIGS. 5A-5B illustrate top and cross-sectional views of an exemplary wearable device including force sensors surrounding the cover structures according to examples of the disclosure.
Figure 5B:
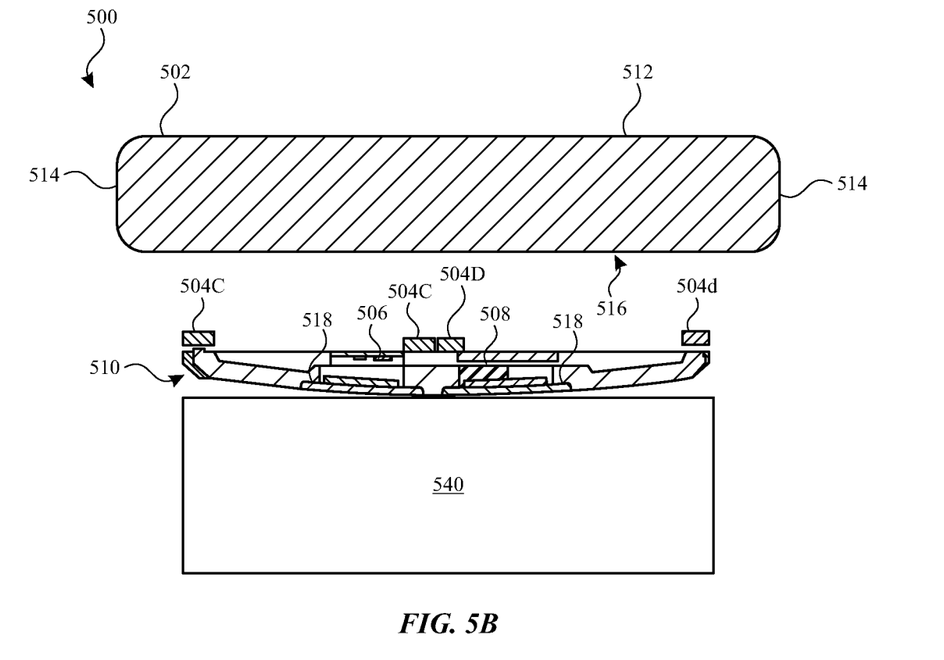

FIGS. 5A-5B illustrate top and cross-sectional views of an exemplary wearable device including force sensors surrounding the cover structures according to examples of the disclosure. Device 500 can include housing 502. Coupled to housing 502 can be force sensor 504a, force sensor 504b, force sensor 504c, and force sensor 504d. Device 500 can further include PPG sensor system 510. PPG sensor system 522 can include light emitters 506 and photodetector 508. In some examples, the force sensing can include a force sensor located around the perimeter (i.e., surrounding) each cover structure 518. Examples of the disclosure can include back plate 510, which force sensor 504a, force sensor 504b, force sensor 504c, and force sensor 504d can be disposed on. In some examples, cover structures 518 can be disposed on or attached to back plate 510. Force sensors (e.g., force sensor 504c and force sensor 504d) can be located between housing 502 and back plate 510, as illustrated in FIG. 5B.

In some instances, internal tissue force can applied pressure to back plate 510 (or housing 502). Back plate 510 (or housing 502) can transfer the applied force to the force sensors. The force sensors can detect the applied force (e.g., internal tissue force) and can generate a signal (e.g., a "force" signal) indicative of the amount of force applied. In some examples, the force signal can indicate whether or not a force has been applied without any information about the amount of force applied.

In some examples, each of the force sensors can be independently operable (e.g., independently biased) such that each sensor can measure different regions (e.g., region coupled to the corresponding optical component) of device 500 subject to force. Each force sensor can be capable of discerning different amounts of force applied to different regions of device 500 and/or different amount of internal forces in skin 540. For example, more force may be applied to one side (e.g., left side, closest to where LED1 can be located) than another side (e.g., right side, closest to where LED2 can be located). Force sensor 504c can generate a force signal with a higher intensity than force sensor 504a.

Methods for operating wearable devices capable of obtaining PPG signals and detecting contact to a user are further disclosed herein. In some variations, the methods generally include operating the wearable device in a contact mode; detecting a force signal using a force sensor while the wearable device operates in the contact mode; operating the wearable device in a physiological signal mode; detecting a PPG signal using a PPG sensor while the wearable device operates in the physiological signal mode; and conditioning or disqualifying the PPG signal using the force signal. In some instances, conditioning includes filtering the force signal from the PPG signal. The contact mode and physiological signal mode may be operated continuously, intermittently, simultaneously, or upon activation by a user. When activated to work in the contact mode, the wearable device will generally operate to obtain a force signal from the force sensor and determine whether sufficient force is being applied by the wearable device and/or whether the device is in a worn or an unworn state. As previously stated, the force signal may be used to provide information on whether the wearable device should be repositioned on a body area and/or whether the amount of pressure exerted by the wearable device should be decreased or increased so that it can operate in a more desirable pressure range. When activated to work in the physiological signal mode, the wearable device will generally operate to obtain a PPG signal from the PPG sensor(s).

In one variation of operating the wearable device, if no force signal is detected or if the detected force signal is below a minimum force threshold, the wearable device is turned to a locked state. Some variations of the wearable device may be configured to automatically turn to a locked state when the detected force signal is below a minimum force threshold. In other variations, a manual mechanism, e.g., a push button can be used to perform those functions after the user is alerted to turn the wearable device to a locked state.

In another variation, if the detected force signal is above a maximum force threshold during a time period, the PPG signal from the same time period is disqualified. In yet a further variation, if the detected force signal is below a minimum force threshold, the wearable device indicates to the user to increase the pressure from the wearable device against the user's skin. Likewise, if the detected force signal is above a maximum force threshold, the wearable device can indicate to the user to decrease the pressure from the wearable device against the user's skin. Any suitable alert may be used as an indicator. For example, the alert may be a visual, audible, or mechanical (e.g., vibration) indicator. Feedback from the force sensor can be obtained in real-time. When the wearable device is a wrist-watch having a band, the force signal may indicate or suggest that the watch be moved to a different location (e.g., in a location on the forearm other than the wrist) or that the band be tightening or loosened to increase or decrease the pressure, respectively, against the user's skin. The methods for operating wearable devices are generally performed to obtain a PPG signal that provides data related to heart rate of a user.

The PPG signals may be obtained from a user by attaching a wearable device to the user, the wearable device comprising a PPG sensor system and a force sensor; detecting a PPG signal using the PPG sensor system; detecting a force signal using the force sensor; and conditioning the PPG signal by filtering the force signal from the PPG signal. In other variations, methods for obtaining PPG signals of a user comprise attaching a wearable device to the user, the wearable device comprising a PPG sensor system and a force sensor; detecting a PPG signal using the PPG sensor system; simultaneously detecting a force signal using the force sensor; and disqualifying the PPG signal if the force signal is above a maximum force threshold.

When two light emitters and two photodetectors are employed, the PPG sensors may operate to obtain a physiological or PPG signal by: emitting light from a first light emitter; receiving at the first photodetector first light information from the first light emitter; emitting light from a second light emitter; receiving at the second photodetector second light information from the second light emitter; computing first and second scaling factors based on the first and second light information; and computing a heart rate signal based on the first light information added to the second light information, the first and second light information each being scaled by the respective first and second scaling factors.

Additionally or alternatively, the first light emitter may be located a first distance from the first photodetector along a surface of the wearable device, and the second light emitter may be located a second distance from the second photodetector along a surface of the wearable device; wherein the second distance may be greater than the first distance.

Additionally or alternatively, an emission pattern of the first light emitter may have a first angle of emission and an emission pattern of the second light emitter may have a second angle of emission; wherein the second angle of emission may be more acute than the first angle of emission. Additionally or alternatively, the computing of the first and second scaling factors may include optimization based on a previously computed heart rate signal.

Additionally or alternatively to one or more of the variations discussed above, the first light emitter may emit light having a first wavelength and the second light emitter may emit light having a second wavelength, the first wavelength being different from the second wavelength.

Additionally or alternatively to one or more of the examples discussed above, the first light emitter may emit light during a first period and the second light emitter may emit light during a second period different from the first period, and wherein the first light information may be received during the first period and the second light information may be received during the second period.

As previously stated, a processor included in the wearable device will generally be configured to execute algorithms for carrying out the various methods described herein and control the reception and manipulation of input and output data between components of wearable device, e.g., the light emitters, photodetectors, and force sensor(s). The processor can be a single-chip processor or can be implemented with multiple components.

In some variations, the processor together with an operating system can operate to execute computer code and produce and use data. The computer code and data can reside within a program storage block that can be operatively coupled to the processor. The program storage block can generally provide a place to hold data that is being used by the operating system. The program storage block can be any non-transitory computer-readable storage medium, and can store, for example, history and/or pattern data relating to PPG signal values measured by one or more photodetectors. By way of example, the program storage block can include Read-Only Memory (ROM), Random-Access Memory (RAM), a hard disk drive and/or the like. The computer code and data could also reside on a removable storage medium and loaded or installed onto the operating system when needed. Removable storage mediums include, for example, CD-RM, DVD-ROM, Universal Serial Bus (USB), Secure Digital (SD), Compact Flash (CF), Memory Stick, Multi-Media Card (MMC), and a network component.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

The present disclosure recognizes that personal information data, including biometric data, in the present technology, can be used to the benefit of users. For example, the use of biometric authentication data can be used for convenient access to device features without the use of passwords. In other examples, user biometric data is collected for providing users with feedback about their health or fitness levels. Further, other uses for personal information data, including biometric data that benefit the user are also contemplated by the present disclosure.

The present disclosure further contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure, including the use of data encryption and security methods that meets or exceeds industry or government standards. For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

Despite the foregoing, the present disclosure also contemplates embodiments in which users selectively block the use of, or access to, personal information data, including biometric data. That is, the present disclosure contemplates that hardware and/or software elements can be provided to prevent or block access to such personal information data. For example, in the case of biometric authentication methods, the present technology can be configured to allow users to optionally bypass biometric authentication steps by providing secure information such as passwords, personal identification numbers (PINS), touch gestures, or other authentication methods, alone or in combination, known to those of skill in the art. In another example, users can select to remove, disable, or restrict access to certain health-related applications collecting users' personal health or fitness data.

A wearable device is disclosed. The wearable device can comprise: a housing; one or more photoplethysmographic (PPG) sensors for detecting light and generate a PPG signal indicative of the detected light; one or more force sensors, each force sensor configured to detect a force applied to the force sensor and generate a force signal indicative of the applied force; and logic configured to: receive the PPG signal and the force signal, condition the PPG signal using the force signal, and determine one or more physiological information from the conditioned PPG signal. Additionally or alternatively, in some examples, the applied force correlates to an internal tissue force. Additionally or alternatively, in some examples, each force sensor is operatively coupled to a separate PPG sensor. Additionally or alternatively, in some examples, the force sensor comprises a thin film flexible printed circuit, a flexible membrane, a flexible film, a strain-gauge, a load cell, a piezoelectric material, a ferromagnetic material, an optical fiber, a foil layer, an electrode, or combinations thereof. Additionally or alternatively, in some examples, each force sensor is independently operable from the other force sensors. Additionally or alternatively, in some examples, the one or more force sensors are located between one or more edges of the device and the one or more PPG sensors. Additionally or alternatively, in some examples, the wearable device further comprises: a back plate attached to the housing, wherein the one or more PPG sensors are located in the back plate, and the one or more force sensors are located between the back plate and the housing. Additionally or alternatively, in some examples, the wearable device further comprises: a back plate attached to the housing, wherein the one or more PPG sensors are located in the back plate, the housing is located on one side of the back plate, and the one or more force sensors are located on an opposite side of the back plate. Additionally or alternatively, in some examples, the wearable device further comprises: one or more light emitters configured to generate light, wherein the one or more PPG sensors and the one or more light emitters are included in a plurality of optical components, and each force sensor surrounds one of the plurality of optical components. Additionally or alternatively, in some examples, the wearable device further comprises: one or more light emitters configured to generate light, wherein the one or more PPG sensors and the one or more light emitters are included in a plurality of optical components, and each force sensor is located around a side of one of the plurality of optical components. Additionally or alternatively, in some examples, at least two of the one or more force sensors are electrically coupled together.

A method for operating a wearable device is disclosed. The method can comprise: contacting at least a portion of the wearable device to a skin of a user; detecting one or more forces applied to one or more force sensors included in the wearable device; generating one or more force signals indicative of the detected one or more applied forces; operating the wearable device in a physiological signal mode; determining one or more PPG signals using one or more PPG sensors while the wearable device operates in the physiological signal mode; and conditioning or disqualifying the one or more PPG signals using the one or more force signals. Additionally or alternatively, in some examples, conditioning the PPG signal comprises filtering the one or more force signals from the one or more PPG signals. Additionally or alternatively, in some examples, the method further comprises: switching the wearable device to a locked state when either no force signal is detected or when the detected one or more force signals is below a minimum force threshold. Additionally or alternatively, in some examples, the method further comprises: disqualifying the one or more PPG signals from a time period when the one or more force signals is above a maximum force threshold during the time period. Additionally or alternatively, in some examples, the method further comprises: determining whether the detected one or more force signals are below a minimum force threshold; and indicating to the user to change an external pressure applied from the wearable device to the skin of the user. Additionally or alternatively, in some examples, the method further comprises: determining whether the detected one or more force signals are below a minimum force threshold; and indicating to the user to reposition the wearable device on a body area of the user. Additionally or alternatively, in some examples, the method further comprises: coupling at least two of the one or more force sensors together; and generating an aggregate force signal, wherein the aggregate force signal is included in the one or more force signals. Additionally or alternatively, in some examples, the method further comprises: measuring a differential force signal from two of the one or more force sensors; and generating an aggregate force signal, wherein the aggregate force signal is included in the one or more force signals.

A method for obtaining PPG signals of a user is disclosed. The method can comprise: attaching a wearable device to the user, the wearable device comprising a PPG sensor system and a force sensor; detecting a PPG signal using the PPG sensor system; simultaneously detecting a force signal using the force sensor; and disqualifying the PPG signal if the force signal is above a maximum force threshold.

The invention claimed is:

1. A method for obtaining a photoplethysmographic (PPG) signal of a user comprising:
    attaching a wearable device to the user, the wearable device comprising a PPG sensor system and a force sensor;
    detecting an input signal using the PPG sensor system;
    detecting a force signal using the force sensor, wherein the detection of the input signal is simultaneous with the detection of the force signal;
    determining, during a time, whether the force signal includes a motion artifact;
    in the event the force signal includes the motion artifact, disqualifying the input signal during the time; and
    in the event the force signal does not include the motion artifact, using the input signal as the PPG signal during the time.

2. The method of claim 1, wherein:
    the method further comprises, in the event the force signal does not include the motion artifact, conditioning the input signal by removing a part of the force signal from the input signal; and
    the conditioned input signal is used as the PPG signal.

3. The method of claim 2, further comprising determining a heart rate from the PPG signal.

4. The method of claim 2, further comprising determining an oxygen saturation from the PPG signal.

5. The method of claim 2, wherein the conditioning of the input signal includes filtering the force signal from the input signal.

6. The method of claim 1, further comprising notifying or alerting the user to decrease an external pressure applied to the wearable device.

7. The method of claim 6, wherein the notification or the alert includes an indication to loosen a band of the wearable device, the band used to attach the wearable device to the user.

8. The method of claim 1, further comprising:
    determining, during the time, whether the force signal indicates a maximum force; and
    in the event the force signal indicates the maximum force, disqualifying the input signal during the time.

9. The method of claim 1, wherein the detection of the force signal using the force sensor includes detecting a force applied between a back plate and a housing of the wearable device.

10. The method of claim 1, wherein the detection of the force signal using the force sensor includes detecting a force applied directly to the force sensor by the user.

11. The method of claim 1, wherein:
    the input signal is a first input signal;
    the force signal is a first force signal;
    the force sensor is a first force sensor
    the first force signal corresponds to a first region of the wearable device; and the method further comprises:
        detecting a second input signal using the PPG sensor system;
        detecting a second force signal using a second force sensor, the second force signal corresponding to a second region of the wearable device; and
        disqualifying the second input signal if the second force signal is at a maximum force value.

12. The method of claim 11, further comprising discerning between force on the first region and force on the second region of the wearable device.

13. The method of claim 1, further comprising determining whether or not the wearable device is in contact with the user.

14. The method of claim 13, further comprising switching the wearable device to at least one of a locked state or a low power mode in accordance with a determination that the wearable device is not in contact with the user.

15. The method of claim 1, further comprising notifying or alerting the user to increase an external pressure applied to the wearable device.

16. The method of claim 15, wherein the notification or the alert includes an indication to reposition the wearable device on a body area of the user.

17. The method of claim 16, wherein the indication includes a prompt to move the wearable device in a specific direction.

18. The method of claim 15, wherein the notification or the alert includes an indication to tighten a band of the wearable device, the band used to attach the wearable device to the user.

19. The method of claim 1, wherein the force signal is an aggregated signal generated from at least two force sensors.

20. The method of claim 1, wherein the force signal is a differential force signal generated from at least two force sensors.

21. The method of claim 1, further comprising determining whether the wearable device is contacting the user based on the detected force signal.

* * * * *